(12) United States Patent
Jaworek et al.

(10) Patent No.: US 8,647,261 B2
(45) Date of Patent: Feb. 11, 2014

(54) BODY CAVITY ACCESS TUBE ASSEMBLY AND METHOD OF USE

(76) Inventors: Jacqueline Anna Jaworek, Bloomington, IN (US); Christopher D. Bosel, Bloomington, IN (US); Eric John Trueblood, Bloomington, IN (US)

( * ) Notice: Subject to any disclaimer, the term of this patent is extended or adjusted under 35 U.S.C. 154(b) by 118 days.

(21) Appl. No.: 13/366,710

(22) Filed: Feb. 6, 2012

(65) Prior Publication Data

US 2013/0204087 A1 Aug. 8, 2013

(51) Int. Cl.
*A61B 1/00* (2006.01)

(52) U.S. Cl.
USPC ............ 600/114; 600/121; 600/124; 600/125

(58) Field of Classification Search
USPC ......................................... 600/114, 121–125
See application file for complete search history.

(56) References Cited

U.S. PATENT DOCUMENTS

| | | | | |
|---|---|---|---|---|
| 4,607,619 A | * | 8/1986 | Seike et al. | 600/106 |
| 4,784,117 A | * | 11/1988 | Miyazaki | 600/114 |
| 4,821,398 A | | 4/1989 | Hillstead | |
| 4,878,485 A | * | 11/1989 | Adair | 600/122 |
| 5,054,821 A | | 10/1991 | Hillstead | |
| 5,078,483 A | * | 1/1992 | Herzberg | 359/510 |
| 5,237,984 A | * | 8/1993 | Williams et al. | 600/124 |
| 5,242,398 A | | 9/1993 | Knoll et al. | |
| 5,301,657 A | | 4/1994 | Lafferty et al. | |
| 5,496,259 A | * | 3/1996 | Perkins | 600/124 |
| 5,651,771 A | | 7/1997 | Tangherlini et al. | |
| 5,715,815 A | * | 2/1998 | Lorenzen et al. | 128/207.14 |
| 6,231,514 B1 | | 5/2001 | Lowe et al. | |
| 7,510,568 B2 | * | 3/2009 | Bleam et al. | 607/105 |
| 7,854,728 B2 | | 12/2010 | Boyle, Jr. | |

\* cited by examiner

*Primary Examiner* — Matthew J Kasztejna
(74) *Attorney, Agent, or Firm* — Liell & McNeil

(57) ABSTRACT

A body cavity access tube assembly includes a body cavity access tube having an external surface. A collapsible protective sleeve is positioned over the external surface and has a proximal end attached to the body cavity access tube and a distal end attached to a repositioning device The repositioning device is supported on the external surface of the body cavity access tube and has a released configuration wherein the repositioning device and the distal end of the collapsible protective sleeve are movable relative to a longitudinal axis of the body cavity access tube. The repositioning device also has an engaged configuration wherein the repositioning device and the distal end of the collapsible protective sleeve have a fixed position relative to the longitudinal axis of the body cavity access tube.

18 Claims, 5 Drawing Sheets

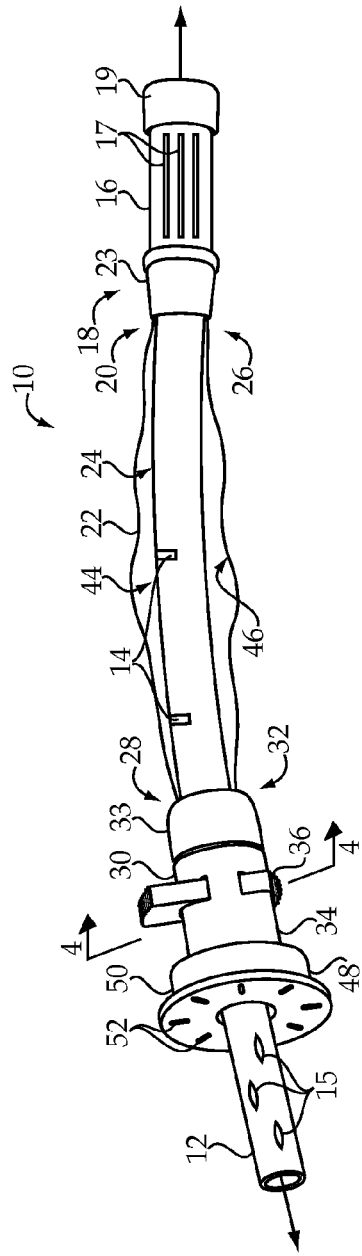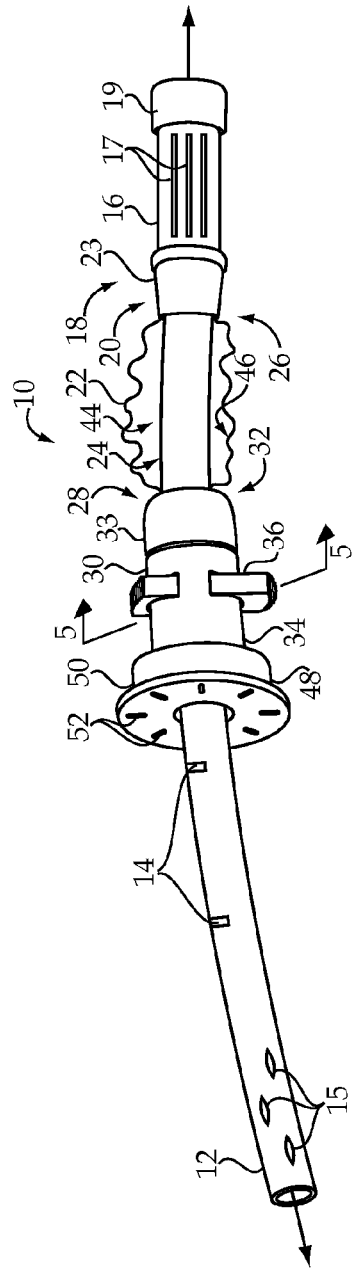
Figure 1
Figure 2

BODY CAVITY ACCESS TUBE ASSEMBLY AND METHOD OF USE

TECHNICAL FIELD

The present disclosure relates generally to a tube assembly for accessing a body cavity, and more particularly to a body cavity access tube assembly having a shielded volume that is adjustable in length.

BACKGROUND

A medical thorascopy, or pleuroscopy, is a medical procedure used by a clinician to examine the pleural cavity and thoracic cavity. During the procedure, a visualization device, such as an endoscope, is inserted into the patient through a relatively small percutaneous puncture site. Such a procedure may be performed in a number of settings, including an operating room and an endoscopy suite, and may be performed under general anesthesia or sedation with local anesthesia. Depending on what is shown during the thorascopy, one or more associated pleural space procedures, such as biopsy, drainage, and chemical pleurodesis, may be required. The associated procedure may require an additional percutaneous puncture site, independent from the puncture site used for the thorascopy, and may require the insertion of a chest tube, or pleural port, to facilitate the procedure. One of the major risks associated with these procedures, particularly where multiple insertion sites are needed, is infection, which can occur if bacteria are present on any of the tubes or devices inserted into the patient.

The present disclosure is directed toward one or more of the problems set forth above.

SUMMARY OF THE DISCLOSURE

In one aspect, a body cavity access tube assembly includes a body cavity access tube having an external surface. A collapsible protective sleeve is positioned over a segment of the external surface and has a proximal end attached to the body cavity access tube at a first attachment. A distal end of the collapsible protective sleeve is attached to a repositioning device at a second attachment. A shielded volume is defined by the external surface of the body cavity access tube, an internal surface of the collapsible protective sleeve, the first attachment, and the second attachment. The repositioning device is supported on the external surface of the body cavity access tube and has a released configuration wherein the repositioning device and the distal end of the collapsible protective sleeve are movable relative to a longitudinal axis of the body cavity access tube. The repositioning device also has an engaged configuration wherein the repositioning device and the distal end of the collapsible protective sleeve have a fixed position relative to the longitudinal axis of the body cavity access tube. The collapsible protective sleeve has an expanded configuration wherein the shielded volume has an expanded length, and a collapsed configuration wherein the shielded volume has a collapsed length that is less than the expanded length.

In another aspect, a method of accessing a body cavity using a body cavity access tube assembly includes a step of inserting a distal segment of a body cavity access tube through a body wall and into the body cavity. A position of a repositioning device and a distal end of a collapsible protective sleeve are fixed relative to the body wall. After the repositioning device is moved from an engaged configuration to a released configuration, the body cavity access tube is moved in an axial direction relative to the body wall, the repositioning device, and the distal end of the collapsible protective sleeve, and a length of a shielded volume is changed. The repositioning device is then moved from the released configuration to the engaged configuration.

BRIEF DESCRIPTION OF THE DRAWINGS

FIG. 1 is perspective view of a body cavity access tube assembly shown in a first configuration, according to the present disclosure;

FIG. 2 is a perspective view of the body cavity access tube assembly of FIG. 1 shown in a second configuration, according to the present disclosure;

DETAILED DESCRIPTION

Figure 3:
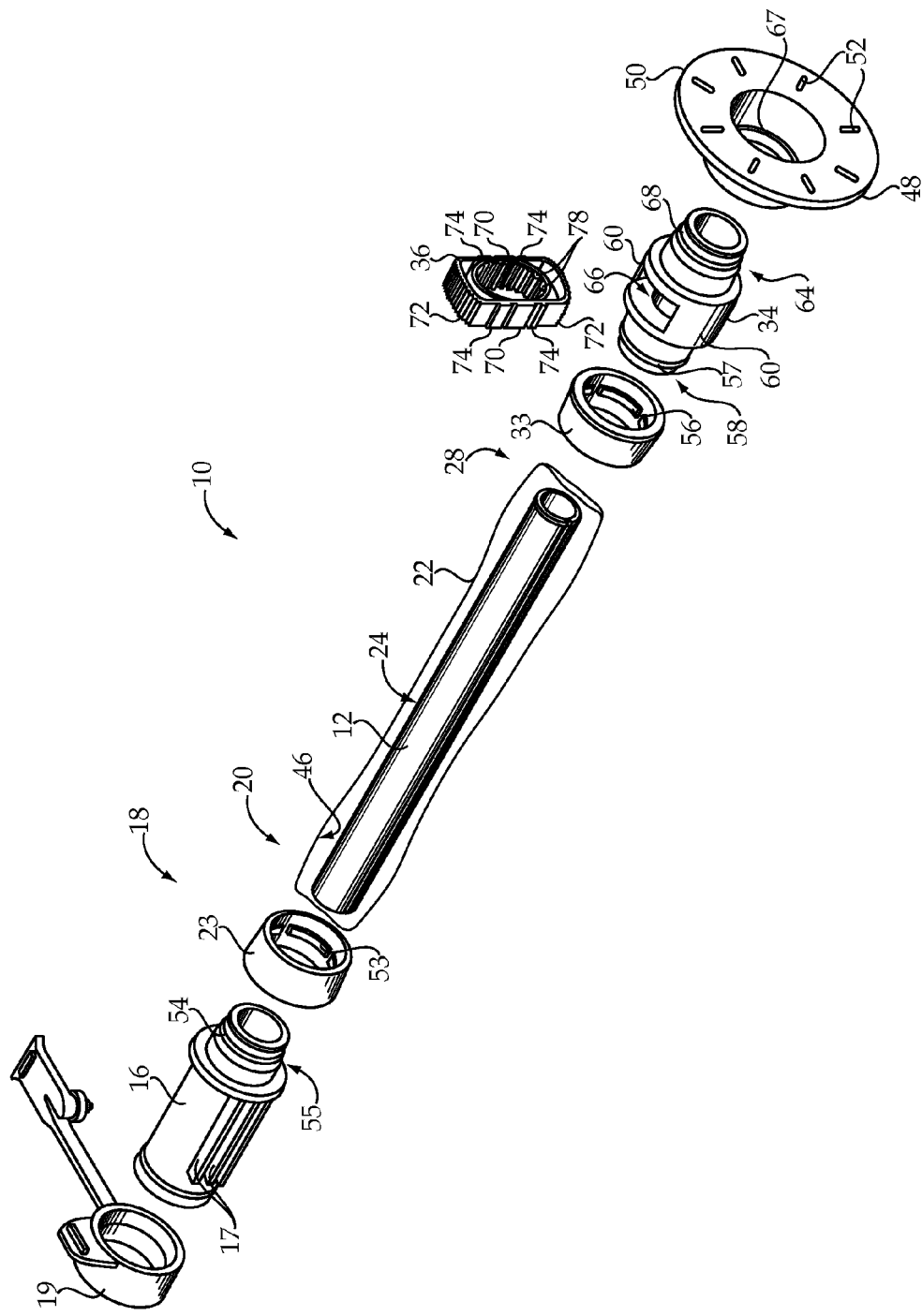
FIG. 3 is an exploded view of the body cavity access tube assembly of FIGS. 1 and 2, according to the present disclosure.

Referring to FIG. 1, there is shown a body cavity access tube assembly 10 according to the present disclosure. The body cavity access tube assembly 10 may be used to access a human body cavity, such as a ventral body cavity. For example, the body cavity access tube assembly 10 may be used to access the thoracic cavity and pleural cavity and, therefore, may also be referred to as a chest tube assembly or pleural port assembly. Although the body cavity access tube assembly 10 will be discussed herein with reference to an endoscopic pleuroscopy, it should be appreciated that the present disclosure may be applicable to other medical tubes and procedures.

The body cavity access tube assembly 10 may include a body cavity access tube 12 having a hollow, tubular body. The body cavity access tube 12, which may be transparent, may be made from any common medical tube material, such as, for example, a plastic, rubber, silicone, or Teflon material, and may exhibit both firmness and flexibility. Materials as well as dimensions may vary depending on the particular application. However, according to one embodiment, the body cavity access tube 12 may have an outer diameter ranging from about 8 French (FR) to about 36 FR and, according to a specific embodiment, may have an outer diameter of about 28 FR. Further, the body cavity access tube 12 may be about 30 centimeters (cm) to about 50 cm in length. According to most embodiments, the body cavity access tube 12 may have a length to diameter ratio of about 50 to 1.

According to some embodiments, the body cavity access tube 12 may include a plurality of indicators 14 corresponding to an inserted length of the body cavity access tube 12. For example, the indicators 14 may include markings on the body cavity access tube 12 that correspond to an inserted length of the body cavity access tube 12 and, thus, assist in placement of the body cavity access tube 12. According to a specific embodiment, the indicators 14 may be used to position one or more of a plurality of drainage ports 15 at a desired position within a body cavity. As should be appreciated, the body cavity access tube 12 may include any number of drainage ports 15, or side ports, depending on the intended use of the body cavity access tube 12. For particular procedures, such as exploratory or diagnostic procedures, the body cavity access tube 12 may not require and, thus, may not be provided with drainage ports 15. Although not shown or required, the body cavity access tube 12 may also include a curved distal tip, as is common in a conventional chest tube design.

An adapter hub 16 may be positioned at, or may be integral with, a proximal end 18 of the body cavity access tube 12. In the present disclosure, "proximal" will be used to refer to the end of a component or feature that is closest to a clinician, while "distal" is used to refer to a component or feature that is farthest away from the clinician. Such meanings are consistent with conventional use of the terms and, as such, should be understood by those skilled in the art. The adapter hub 16 may be utilized as a gripping device and/or may be used to attach other tubes or devices to the body cavity access tube 12. Accordingly, the adapter hub 16 may include one or more sets of ridges 17, or gripper strips, extending along a length of the adapter hub 16 to assist in maintaining a grip on the body cavity access tube 12. Further, a rubber cap, or seal, 19 may be provided at a proximal end of the adapter hub 16. The cap 19 may be removed when the body cavity access tube 12 is used for drainage, and, further, may be provided with an opening therethrough for advancing scopes or other tubes through the cap 19, adapter hub 16, and body cavity access tube 12, as necessary. As should be appreciated, the cap 19 may assist with sealing the body cavity access tube 12 while a scope or other device is inserted therethrough.

A proximal end 20 of a collapsible protective sleeve 22 may be attached to the adapter hub 16 using any known attachment means, such as, for example, clips, clamps, or the like. According to the exemplary embodiment, the collapsible protective sleeve 22 may be attached to the adapter hub 16 using a snap cap 23, which will be shown in greater detail in FIG. 3. The collapsible protective sleeve 22 may be made from a flexible film, such as, for example, a medical grade polyethylene film, and may be positioned over a segment of an external surface 24 of the body cavity access tube 12. The proximal end 20 may be attached at a first attachment 26, while a distal end 28 of the collapsible protective sleeve 22 may be attached to a repositioning device 30 at a second attachment 32. For example, the collapsible protective sleeve 22 may be attached to the repositioning device 30 using a snap cap 33, or other suitable attachment means. The "attachments," as used herein, may refer to attachments of open ends of the collapsible protective sleeve 22 that may facilitate a protected or shielded environment within the collapsible protective sleeve 22, as will be described below.

The repositioning device 30 is supported on the external surface 24 of the body cavity access tube 12 and generally includes a tubular housing 34 and a retaining clip 36, both of which may be molded of a resilient material, such as a high strength plastic. The repositioning device 30 is shown in a released configuration in FIG. 1 wherein the repositioning device 30 and the distal end 28 of the collapsible protective sleeve 22 are movable relative to a longitudinal axis A of the body cavity access tube 12. In an engaged configuration, shown in FIG. 2, the repositioning device 30 and the distal end 28 of the collapsible protective sleeve 22 have a fixed position relative to the longitudinal axis A of the body cavity access tube 12.

The body cavity access tube assembly 10 also includes a shielded volume 44, which may serve to reduce the risk of bacteria entering the patient body along the external surface 24 of the body cavity access tube 12. The shielded volume 44 may be defined by the external surface 24 of the body cavity access tube 12, an internal surface 46 of the collapsible protective sleeve 22, the first attachment 26, and the second attachment 32. The collapsible protective sleeve 22 has an expanded configuration, shown in FIG. 1, wherein the shielded volume 44 has an expanded length (relative to the longitudinal axis A), and a collapsed configuration, shown in FIG. 2, wherein the shielded volume 44 has a collapsed length (relative to the longitudinal axis A) that is less than the expanded length. As should be appreciated, the collapsible protective sleeve 22 may fold onto itself as it is collapsed and, thus, collapse to a relatively short length.

Although not shown in the exemplary embodiment, modifications to the body cavity access tube assembly 10 could be made to achieve and maintain a sterile environment within the shielded volume 44. For example, seals or gaskets could be added at the first and second attachments 26 and 32 to form air-tight attachments. Known sterilization methods may also be used in an effort to maintain a shielded or even sterile environment along the exterior surface 24 of the body cavity access tube 12. According to some embodiments, an antimicrobial coating may be provided on all or a portion of the external surface 24 of the body cavity access tube 12.

Figure 6:
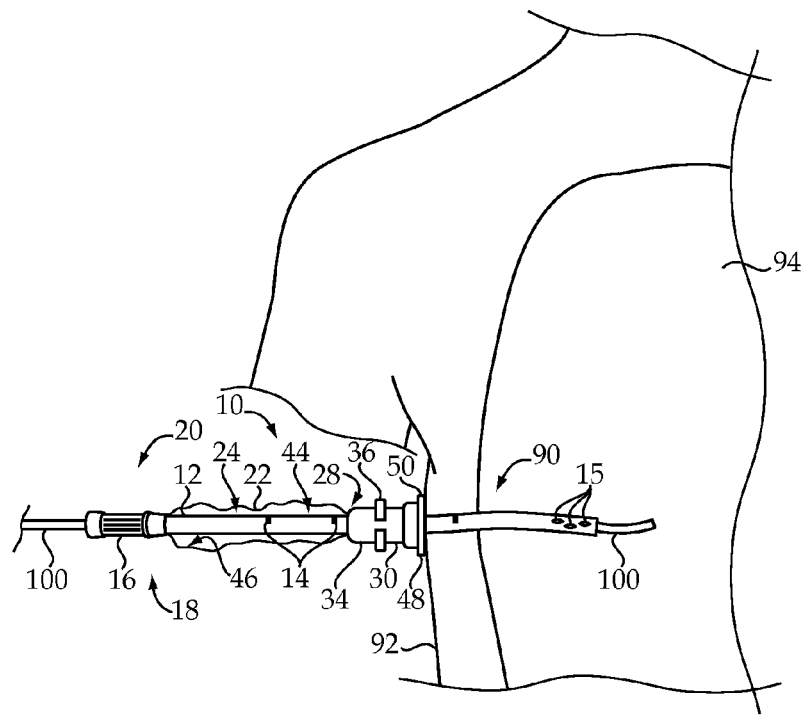
FIG. 6 is a simplified diagrammatic view of one stage of a body cavity access procedure, according to one aspect of the present disclosure.
Figure 7:
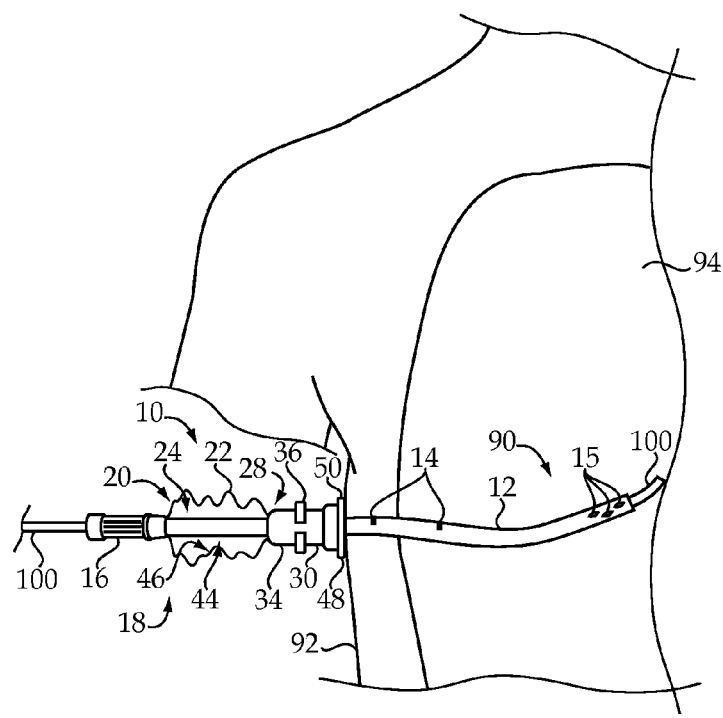
FIG. 7 is a simplified diagrammatic view of another stage of a body cavity access procedure, according to one aspect of the present disclosure.
Figure 8:
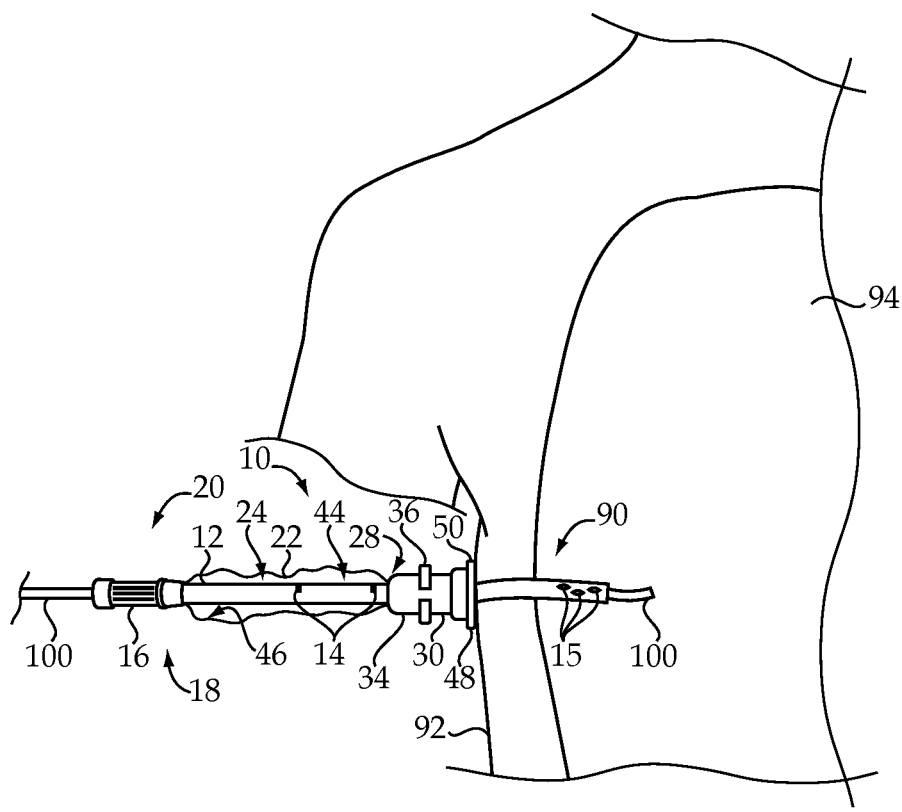
FIG. 8 is a simplified diagrammatic view of yet another stage of a body cavity access procedure, according to one aspect of the present disclosure.

The body cavity access tube assembly 10 may also include a body wall attachment mechanism 48 configured to anchor the repositioning device 30 to a body wall (shown in FIGS. 6-8). According to the exemplary embodiment, the body wall attachment mechanism 48, which may also serve to anchor the body cavity access tube assembly 10 to the body wall, may include an annular attachment flange 50. According to the exemplary embodiment, the body wall attachment mechanism 48, which may, for example, be made from a plastic or rubber material, may be affixed to the body by threading sutures through holes 52 of the annular attachment flange 50 and skin of the patient to limit movement of the repositioning device 30 relative to the patient. As such, the body wall attachment mechanism 48 may also be referred to generally as suture wings. Although a specific attachment mechanism is shown, it should be appreciated that alternative attachment means are contemplated. Further, it should be appreciated that the body wall attachment mechanism 48 may be integral with or a separate component from the repositioning device 30. According to some embodiments, it may be desirable to have a rotating attachment so that the orientation of the repositioning device 30 may be changed during a procedure, if necessary.

The components of the exemplary embodiment of the body cavity access tube assembly 10 are shown in greater detail in the exploded view of FIG. 3. As shown, the snap cap 23 may include one or more protrusions 53 formed on the inner surface of the snap cap 23 that are shaped to engage a circumferential groove 54 of the adapter hub 16. According to the exemplary embodiment, the proximal end 20 of the collapsible protective sleeve 22 may be secured over a distal segment 55 of the adapter hub 16 using the snap cap 23. The additional snap cap 33 may include one or more protrusions 56 for engaging a circumferential groove 57 of the tubular housing 34. According to the exemplary embodiment, the distal end 28 of the collapsible protective sleeve 22 may be secured over a proximal segment 58 of the tubular housing 34 using the snap cap 33. Alternatively, a fastener, such as an o-ring, may be positioned over the distal end 28 of the collapsible protective sleeve 22 and within the circumferential groove 57 to form the second attachment 32.

The tubular housing 34 may be generally shaped and sized to facilitate movement of the repositioning device 30 relative to the body cavity access tube 12. Specifically, the tubular housing 34 may have an inner diameter sized to correspond to an outer diameter of the body cavity access tube 12 such that the repositioning device 30 may slide along the external surface 24 of the body cavity access tube 12 in the released configuration of the repositioning device 30. Further, as will be described below, the tubular housing 34 may include a pair of sidewalls 60 that attach the proximal segment 58 of the housing 34 to a distal segment 64 of the housing 34, and facilitate repositioning of the retaining clip 36 with respect to the tubular housing 34. Specifically, an opening 66 defined by the proximal and distal segments 58 and 64 and the sidewalls 60 may be shaped and sized to receive at least a portion of the retaining clip 36 in the configurations discussed below. The body wall attachment mechanism 48, according to the exemplary embodiment, may include one or more protrusions 67 for engaging a circumferential groove 68 of the distal segment 64 of the tubular housing 34. Of course, other attachment means are also contemplated.

The retaining clip 36 may include a pair of flexible sidewalls 70 spaced from one another and attached at arcuate shaped ends 72. The pair of flexible sidewalls 70 may include a pair of outwardly extending projections 74 that are shaped for engagement with surfaces of the tubular housing 34. The flexible sidewalls 70 may be inwardly deflected to move the retaining clip 36 relative to the tubular housing surfaces, as will be described below. A plurality of inwardly projecting teeth 78, the number of which may vary, extending from an internal surface of the retaining clip 36 may be configured to frictionally engage the external surface 24 of the body cavity access tube 12 in a locked position of the retaining clip 36.

Figure 4:
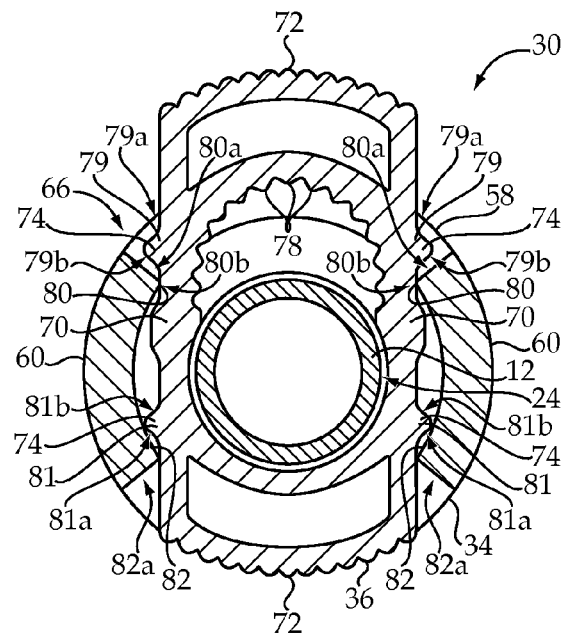
FIG. 4 is a cross sectional view of the body cavity access tube assembly of FIG. 1 taken along lines 4-4, according to one aspect of the present disclosure.

The manner of use of the retaining clip 36 with respect to the tubular housing 34 is best described with reference to FIGS. 4 and 5. Specifically, the pair of flexible sidewalls 70 may be received, at least partially, within the opening 66 of the tubular housing 34 and may be inwardly movable, or deflectable, to permit movement of the retaining clip 36 between an unlocked position, shown in FIG. 4, and a locked position, shown in FIG. 5. More specifically, the retaining clip 36 may be movable to position a first set of outwardly extending projections 79 of the retaining clip 36 at outer positions relative to first shoulders 80 of the tubular housing 34 in the unlocked position of the retaining clip 36, as shown in FIG. 4, while a second set of outwardly extending projections 81 of the retaining clip 36 are positioned at inner positions relative to second shoulders 82 of the tubular housing 34. As should be apparent from the view of FIG. 3, the first and second shoulders 80 and 82 are defined by sidewalls 60 of the tubular housing 34. The retaining clip 36 is also movable to position the first set of projections 79 of the retaining clip 36 at inner positions relative to the first shoulders 80 in the locked position of the retaining clip 36, as shown in FIG. 5, while the second set of projections 81 are positioned at outer positions relative to the second shoulders 82.

More specifically, in the unlocked position of FIG. 4, inner surfaces 79b of the first set of projections 79 may engage outer surfaces 80a of the first shoulders 80, while outer surfaces 81a of the second set of projections 81 engage inner surfaces 82b of the second shoulders 82. In the locked position of FIG. 5, outer surfaces 79a of the first set of projections 79 may engage inner surfaces 80b of the first shoulders 80, while inner surfaces 81b of the second set of projections 81 engage outer surfaces 82a of the second shoulders 82. The retaining clip 36 may be moved between the unlocked and locked positions by urging the flexible sidewalls 70 inward and/or pushing one of the arcuate shaped ends 72 toward the tubular housing 34.

Figure 5:
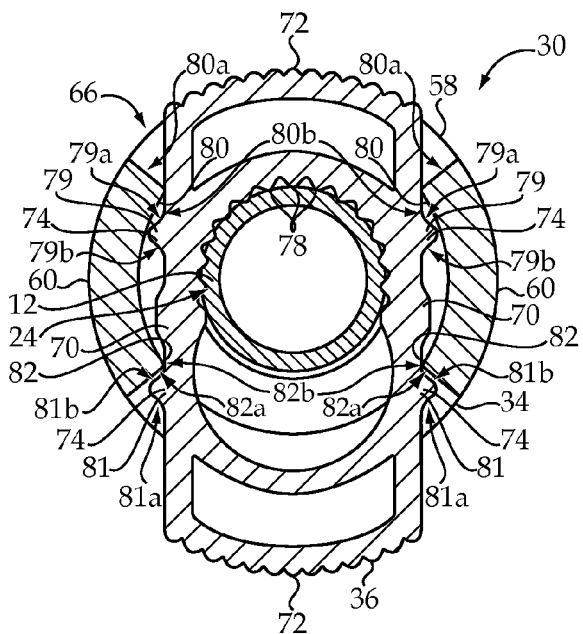
FIG. 5 is a cross sectional view of the body cavity access tube assembly of FIG. 2 taken along lines 5-5, according to another aspect of the present disclosure.

In the locked position of the retaining clip 36, as shown in FIG. 5, the plurality of inwardly projecting teeth 78 may frictionally engage the external surface 24 of the body cavity access tube 12 to fix a position of the body cavity access tube 12 relative to the repositioning device 30 and the distal end 28 of the collapsible protective sleeve 22. The number and shape of the inwardly projecting teeth 78 may be selected to provide the desired frictional engagement and, thus, locking capabilities, without damaging the body cavity access tube 12.

As should be appreciated, the unlocked position of the retaining clip 36 (FIG. 4) may correspond to the released configuration of the repositioning device 30 (FIG. 1), while the locked position (FIG. 5) may correspond to the engaged configuration of the repositioning device 30 (FIG. 2). Therefore, in the unlocked position of the retaining clip 36, the body cavity access tube 12 may be movable relative to the repositioning device 30, and the collapsible protective sleeve 22 may be moved between expanded and collapsed configurations. In the locked position of the retaining clip 36, the body cavity access tube 12 is fixed relative to the repositioning device 30. As a result, the length of the shielded volume 44 is also fixed in the locked position of the retaining clip 36. Although a specific repositioning device 30 is shown, it should be appreciated that alternative devices performing the function of repositioning device 30 may be used with the body cavity access tube assembly 10.

According to a specific embodiment, which may incorporate the use of the body cavity access tube assembly 10 in an exploratory procedure, the body cavity access tube 12 may be a multi-stiffness tube. Specifically, a distal segment 90, shown in FIGS. 6-8, and the proximal end 18 of the body cavity access tube 12 may be relatively soft or flexible to provide patient comfort, while a middle section, between the distal and proximal ends, may be stiffer, or may have an increased durometer, relative to the distal and proximal ends. This stiffer middle section may assist in movement and advancement of the body cavity access tube assembly 10 during an exploratory procedure and, further, may assist in repositioning a flexible endoscope therethrough. According to a specific embodiment, which utilizes a body cavity access tube 12 approximately 40 cm in length, the relatively flexible distal section may extend approximately 9 cm along an axial length of the tube 12, the relatively stiffer middle section may extend approximately 15 cm along the axial length, and the relatively flexible proximal section may be approximately 17 cm in length.

INDUSTRIAL APPLICABILITY

The present disclosure is generally applicable to body cavity access tubes used for percutaneously accessing body cavities. More specifically, the present disclosure finds application in body cavity access procedures that are performed in a variety of sterility controlled and non-sterility controlled environments, including, for example, an operating room, an endoscopy suite, and a hospital room bedside. Further, the present disclosure finds application in body cavity access procedures, such as exploratory procedures and other associated procedures, that may require repositioning of the body cavity access tube during the procedure.

Referring generally to FIGS. 1-8, a body cavity access tube assembly 10 may include a body cavity access tube 12 having a hollow, tubular body. A collapsible protective sleeve 22 may be positioned over a segment of an external surface 24 of the body cavity access tube 12. A proximal end 20 of the collapsible protective sleeve 22 may be attached to an adapter hub 16 at a first attachment 26, while a distal end 28 of the collapsible protective sleeve 22 may be attached to a repositioning device 30 at a second attachment 32. A shielded volume 44 is defined by the external surface 24 of the body cavity access tube 12, an internal surface 46 of the collapsible protective sleeve 22, the first attachment 26, and the second attachment 32.

The repositioning device 30, which is supported on the external surface 24 of the body cavity access tube 12, has a released configuration wherein the repositioning device 30 and the distal end 28 of the collapsible protective sleeve 22 are movable relative to a longitudinal axis A of the body cavity access tube 12, and an engaged configuration wherein the repositioning device 30 and the distal end 28 of the collapsible protective sleeve 22 have a fixed position relative to the longitudinal axis A. An unlocked position of a retaining clip 36 of the repositioning device 30 corresponds to the released configuration, while a locked position of the retaining clip 36, relative to a tubular housing 34 of the repositioning device 30, corresponds to the engaged configuration.

A method of performing a body cavity access procedure on a patient using the body cavity access tube assembly 10, as disclosed herein, will be discussed with specific reference to the simplified diagrammatic drawings of FIGS. 6-8. Initially, as shown in FIG. 6, a distal segment 90 of the body cavity access tube 12 may be inserted through a body wall 92, at an insertion site, using the standard percutaneous entry, or Seldinger, technique. The length indicators 14, described above, may be used initially and throughout the procedure to determine appropriate placement of the distal segment 90 within a body cavity 94. According to the exemplary embodiment, the body cavity 94 may be the thoracic cavity of a patient and, as such, the body cavity access tube assembly 10 may also be referenced as a chest tube assembly or pleural port assembly. However, the body cavity access tube assembly 10 described herein may be applicable to other body cavity access procedures.

After the distal segment 90 of the body cavity access tube 12 is positioned within the body cavity 94, a position of the repositioning device 30 and, thus, the distal end 28 of the collapsible protective sleeve 22 may be fixed relative to the body wall 92. For example, this may include anchoring the repositioning device 30 to the body wall 92 using a body wall attachment mechanism 48, which may or may not be integral with the repositioning device 30. According to a specific example, the body wall attachment mechanism 48 may be affixed to the body wall 92 by threading sutures through holes 52 of an annular attachment flange 50 and skin of the patient to limit movement of the repositioning device 30 relative to the patient. The annular attachment flange 50 may serve to decrease the risk of bacteria entering the patient through the insertion site.

Once the distal segment 90 is positioned or repositioned, as described herein, the body cavity access tube 12 may be used to perform a number of procedures. For example, a scope 100, such as an endoscope or a bronchoscope, which may be flexible or rigid, may be used to help position the body cavity access tube 12 and/or to perform an exploratory procedure. As such, it may be desirable to move the body cavity access tube 12 within the body cavity 94, such as by further inserting and/or withdrawing the tube 12 relative to the body cavity. After performing the exploratory procedures, such as an endoscopic pleuroscopy, it may be necessary to perform one or more associated pleural space procedures, such as, for example, biopsy, drainage, and chemical pleurodesis. Such associated procedures may also be performed using the body cavity access tube assembly 10 and, thus, do not require an additional percutaneous puncture site.

To reposition the body cavity access tube 12, the repositioning device 30 may be moved from an engaged configuration, as shown in FIGS. 2 and 5, to a released configuration, as shown in FIGS. 1 and 4. This may include moving the retaining clip 36 of the repositioning device 30 to an unlocked position relative to the housing 34 of the repositioning device 30, as shown in FIG. 4. As shown, the unlocked position of the retaining clip 36 allows sufficient clearance through the repositioning device 30 to allow sliding movement of the body cavity access tube 12 through the housing 34.

While the repositioning device is in the released configuration, the body cavity access tube 12 may be moved in an axial direction relative to the body wall 92, the repositioning device 30, and the distal end 28 of the collapsible protective sleeve 22. As a result, a length of the shielded volume 44 is changed. For example, the body cavity access tube 12 may be advanced within the body cavity 94, as shown in FIG. 7, thus decreasing the length of the shielded volume 44. Alternatively, the body cavity access tube 12 may be withdrawn from the body cavity 94, as shown in FIG. 8, thus increasing the length of the shielded volume 44. According to some embodiments, a stylet, as is known in the art, may be used with the body cavity access tube assembly 10 to assist in directing the body cavity access tube 12.

After the body cavity access tube 12 has been repositioned, the repositioning device 30 may be moved from the released configuration (FIGS. 1 and 4) to the engaged configuration (FIGS. 2 and 5). This includes moving the retaining clip 36 of the repositioning device 30 to a locked position relative to the housing 34 of the repositioning device 30, as shown in FIG. 5. Moving the retaining clip 36 of the repositioning device 30 to the locked position includes frictionally engaging the external surface 24 of the body cavity access tube 12 with the plurality of inwardly projecting teeth 78 of the retaining clip 36. In the locked position of the retaining clip 36, the body cavity access tube 12 is fixed relative to the repositioning device 30. As a result, the length of the shielded volume 44 is also fixed in the locked position of the retaining clip 36.

The body cavity access tube assembly of the present disclosure provides a shielded volume surrounding the external surface of the body cavity access tube that is adjustable in length. Specifically, the shielded volume may provide a shielded environment surrounding the body cavity access tube that changes in length as the body cavity access tube is inserted and withdrawn relative to the body cavity. This shielded environment surrounding the body cavity access tube reduces the risk of bacteria entering the patient body along the external surface of the body cavity access tube. As such, the body cavity access tube assembly may be used in a variety of environments, including sterility controlled and non-sterility controlled environments. Further, the body cavity access tube assembly may provide a minimally invasive means to perform both exploratory procedures and associated procedures, with visualization by incorporating the use of a scope, via a single percutaneous puncture site.

The body cavity access tube assembly described herein also allows for fixing a length of the shielded volume at any of a continuum of lengths between expanded and collapsed lengths, thus fixing a length of the inserted segment of the body cavity access tube. Further, the repositioning device may be fixed relative to the body wall. Additionally, inadvertent removal and/or insertion beyond a certain length of the body cavity access tube may be reduced by sizing the collapsible protective sleeve a predetermined length less than the length of the body cavity access tube.

It should be understood that the above description is intended for illustrative purposes only, and is not intended to limit the scope of the present disclosure in any way. Thus, those skilled in the art will appreciate that other aspects of the disclosure can be obtained from a study of the drawings, the disclosure and the appended claims.

What is claimed is:

1. A body cavity access tube assembly, comprising:
a body cavity access tube having an external surface;
a collapsible protective sleeve positioned over a segment of the external surface and having a proximal end attached to the body cavity access tube at a first attachment;
a repositioning device supported on the external surface of the body cavity access tube, wherein a distal end of the collapsible protective sleeve is attached to the repositioning device at a second attachment; and
a shielded volume defined by the external surface of the body cavity access tube, an internal surface of the collapsible protective sleeve, the first attachment, and the second attachment;
the repositioning device having a released configuration wherein the repositioning device and the distal end of the collapsible protective sleeve are movable relative to a longitudinal axis of the body cavity access tube, and an engaged configuration wherein the repositioning device and the distal end of the collapsible protective sleeve have a fixed position relative to the longitudinal axis of the body cavity access tube;
the repositioning device further including a retaining clip having flexible sidewalls, and being movable about the body cavity access tube from an unlocked position corresponding to the released configuration, to a locked position corresponding to the engaged configuration and at which the flexible sidewalls frictionally engage the external surface of the body cavity access tube;
the collapsible protective sleeve having an expanded configuration wherein the shielded volume has an expanded length, and a collapsed configuration wherein the shielded volume has a collapsed length that is less than the expanded length.

2. The body cavity access tube assembly of claim 1, further including a body wall attachment mechanism configured to anchor the repositioning device to a body wall.

3. The body cavity access tube assembly of claim 2, wherein the body wall attachment mechanism includes an annular attachment flange.

4. The body cavity access tube assembly of claim 2, wherein the repositioning device includes a tubular housing and the retaining clip is slidable within an opening in the tubular housing from the unlocked position to the locked position.

5. The body cavity access tube assembly of claim 2, further including an adapter hub positioned at a proximal end of the body cavity access tube, wherein the proximal end of the collapsible protective sleeve is attached to the adapter hub.

6. The body cavity access tube assembly of claim 2, wherein the shielded volume has a continuum of lengths between the collapsed length and the expanded length.

7. The body cavity access tube assembly of claim 2, wherein the external surface of the body cavity access tube includes a plurality of indicators corresponding to an inserted length of the body cavity access tube.

8. The body cavity access tube assembly of claim 2, wherein the body cavity access tube is a multi-stiffness tube.

9. A body cavity access tube assembly comprising:
a body cavity access tube having an external surface;
a collapsible protective sleeve positioned over a segment of the external surface and having a proximal end attached to the body cavity access tube at a first attachment;
a repositioning device supported on the external surface of the body cavity access tube, wherein a distal end of the collapsible protective sleeve is attached to the repositioning device at a second attachment; and
a shielded volume defined by the external surface of the body cavity access tube, an internal surface of the collapsible protective sleeve, the first attachment, and the second attachment;
the repositioning device having a released configuration wherein the repositioning device and the distal end of the collapsible protective sleeve are movable relative to a longitudinal axis of the body cavity access tube, and an engaged configuration wherein the repositioning device and the distal end of the collapsible protective sleeve have a fixed position relative to the longitudinal axis of the body cavity access tube;
the collapsible protective sleeve having an expanded configuration wherein the shielded volume has an expanded length, and a collapsed configuration wherein the shielded volume has a collapsed length that is less than the expanded length;
the body cavity access tube assembly further including a body wall attachment mechanism configured to anchor the repositioning device to a body wall;
wherein the body wall attachment mechanism includes an annular attachment flange;
wherein the repositioning device includes a tubular housing and a retaining clip, wherein the retaining clip has an unlocked position corresponding to the released configuration and a locked position corresponding to the engaged configuration;
wherein the retaining clip includes a pair of flexible sidewalls received at least partially within the tubular housing, wherein the pair of flexible sidewalls are inwardly movable to permit movement of the retaining clip between the locked and unlocked positions.

10. The body cavity access tube assembly of claim 9, wherein the pair of flexible sidewalls includes a pair of outwardly extending projections for engagement with outer surfaces of first shoulders of the tubular housing in the unlocked position and inner surfaces of the first shoulders in the locked position.

11. The body cavity access tube assembly of claim 10, wherein the retaining clip includes a plurality of inwardly projecting teeth configured to frictionally engage the external surface of the body cavity access tube in the locked position of the retaining clip.

12. A method of accessing a body cavity using a body cavity access tube assembly, the body cavity access tube assembly including a body cavity access tube having an external surface, a collapsible protective sleeve positioned over a segment of the external surface and having a proximal end attached to the body cavity access tube at a first attachment, a repositioning device supported on the external surface of the body cavity access tube, wherein a distal end of the collapsible protective sleeve is attached to the repositioning device at a second attachment, and a shielded volume defined by the external surface of the body cavity access tube, an internal surface of the collapsible protective sleeve, the first attachment, and the second attachment, the method comprising the steps of:

inserting a distal segment of the body cavity access tube through a body wall and into the body cavity;

fixing a position of the repositioning device and the distal end of the collapsible protective sleeve relative to the body wall;

moving the repositioning device from an engaged configuration to a released configuration;

moving the body cavity access tube in an axial direction relative to the body wall, the repositioning device, and the distal end of the collapsible protective sleeve, and changing a length of the shielded volume; and moving the repositioning device from the released configuration to the engaged configuration;

wherein the step of moving the repositioning device to the released configuration further includes moving a retaining clip of the repositioning device from an unlocked position corresponding to the released configuration, to a locked position corresponding to the engaged configuration at which flexible sidewalls of the retaining clip frictionally engage the external surface of the body cavity access tube.

13. The method of claim 12, wherein the fixing step includes anchoring the repositioning device to the body wall using a body wall attachment mechanism.

14. The method of claim 13, wherein the fixing step further includes attaching an annular attachment flange to the body wall.

15. The method of claim 13, wherein the step of moving the body cavity access tube further includes advancing the body cavity access tube within the body cavity and decreasing the length of the shielded volume.

16. The method of claim 13, wherein the step of moving the body cavity access tube further includes withdrawing the body cavity access tube from the body cavity and increasing the length of the shielded volume.

17. The method of claim 13, further including inserting a scope through the body cavity access tube.

18. The method of claim 12, wherein the step of moving the retaining clip of the repositioning device to a locked position includes frictionally engaging the external surface of the body cavity access tube with a plurality of inwardly projecting teeth of the retaining clip.

* * * * *

UNITED STATES PATENT AND TRADEMARK OFFICE
CERTIFICATE OF CORRECTION

PATENT NO. : 8,647,261 B2  
APPLICATION NO. : 13/366710  
DATED : February 11, 2014  
INVENTOR(S) : Jacqueline Anna Jaworek, Christopher D. Bosel and Eric John Trueblood Page 1 of 1

It is certified that error appears in the above-identified patent and that said Letters Patent is hereby corrected as shown below:

On the title page, item [73] Assignee should read as follows: Cook Medical Technologies LLC Signed and Sealed this  
Nineteenth Day of August, 2014

Michelle K. Lee  
*Deputy Director of the United States Patent and Trademark Office*